(12) United States Patent
Fischvogt et al.

(10) Patent No.: US 9,867,620 B2
(45) Date of Patent: Jan. 16, 2018

(54) ARTICULATION JOINT FOR APPARATUS FOR ENDOSCOPIC PROCEDURES

(71) Applicant: Covidien LP, Mansfield, MA (US)

(72) Inventors: Gregory Fischvogt, Hamden, CT (US); Kevin Sniffin, Danbury, CT (US); Jay Breindel, Kensington, CT (US); Mark Russo, Plantsville, CT (US)

(73) Assignee: COVIDIEN LP, Mansfield, MA (US)

( * ) Notice: Subject to any disclaimer, the term of this patent is extended or adjusted under 35 U.S.C. 154(b) by 701 days.

(21) Appl. No.: 14/172,101

(22) Filed: Feb. 4, 2014

(65) Prior Publication Data
US 2014/0276967 A1    Sep. 18, 2014

Related U.S. Application Data

(60) Provisional application No. 61/783,559, filed on Mar. 14, 2013.

(51) Int. Cl.
| | |
|---|---|
| *A61B 17/12* | (2006.01) |
| *A61B 17/068* | (2006.01) |
| *A61B 17/072* | (2006.01) |
| *A61B 17/064* | (2006.01) |
| *A61B 17/29* | (2006.01) |

(52) U.S. Cl.
CPC ...... *A61B 17/12013* (2013.01); *A61B 17/068* (2013.01); *A61B 17/07207* (2013.01);
(Continued)

(58) Field of Classification Search
CPC ............ A61B 17/12013; A61B 17/068; A61B 17/07207; A61B 2017/0649; A61B 2017/2903; A61B 2017/2927
(Continued)

(56) References Cited

U.S. PATENT DOCUMENTS

| | | |
|---|---|---|
| 3,596,528 A | 8/1971 | Dittrich et al. |
| 3,866,510 A | 2/1975 | Eibes |
| | (Continued) | |

FOREIGN PATENT DOCUMENTS

| | | |
|---|---|---|
| DE | 10300787 A1 | 9/2004 |
| DE | 10 2010 015009 A1 | 10/2011 |
| | (Continued) | |

OTHER PUBLICATIONS

U.S. Appl. No. 13/799,379, filed Mar. 2013, Williams.
(Continued)

*Primary Examiner* — Hemant M Desai
*Assistant Examiner* — Mobeen Ahmed

(57) ABSTRACT

An endoscopic surgical device is provided and includes an endoscopic anchor retaining/advancing assembly including a proximal tube portion and a distal tube portion pivotably connected to one another at an articulation joint; a proximal inner shaft rotatably disposed within the proximal tube portion; a distal inner shaft rotatably disposed within the distal tube portion; and a relatively flexible intermediate drive cable mechanically interconnecting the proximal inner shaft and the distal inner shaft, wherein the intermediate drive cable extends across the articulation joint, wherein the intermediate drive cable defines a central longitudinal axis that is off-set a radial distance from a central longitudinal axis of the proximal tube portion and the distal tube portion.

18 Claims, 7 Drawing Sheets

(52) U.S. Cl.
CPC ............... *A61B 2017/0649* (2013.01); *A61B 2017/2903* (2013.01); *A61B 2017/2927* (2013.01)

(58) Field of Classification Search
USPC ........................................ 227/175.1; 606/139
See application file for complete search history.

(56) References Cited

U.S. PATENT DOCUMENTS

| | | | |
|---|---|---|---|
| 4,350,491 A | 9/1982 | Steuer | |
| 4,884,572 A | 12/1989 | Bays | |
| 5,085,661 A | 2/1992 | Moss | |
| 5,108,411 A | 4/1992 | McKenzie | |
| 5,171,247 A | 12/1992 | Hughett | |
| 5,171,249 A | 12/1992 | Stefanchik | |
| 5,176,306 A | 1/1993 | Heimerl | |
| 5,207,697 A | 5/1993 | Carusillo | |
| 5,228,256 A | 7/1993 | Dreveny | |
| 5,236,563 A | 8/1993 | Loh | |
| 5,246,441 A | 9/1993 | Ross | |
| 5,246,450 A | 9/1993 | Thornton | |
| 5,271,543 A * | 12/1993 | Grant | A61B 17/115 227/179.1 |
| 5,312,023 A * | 5/1994 | Green | A61B 17/07207 227/175.1 |
| 5,330,487 A | 7/1994 | Thornton | |
| 5,344,061 A | 9/1994 | Crainich | |
| 5,348,017 A | 9/1994 | Thornton | |
| 5,356,064 A | 10/1994 | Green | |
| 5,381,943 A | 1/1995 | Allen et al. | |
| 5,382,254 A | 1/1995 | McGarry | |
| 5,398,861 A | 3/1995 | Green | |
| 5,403,327 A | 4/1995 | Thornton | |
| 5,433,721 A * | 7/1995 | Hooven | A61B 17/068 227/175.1 |
| 5,439,468 A | 8/1995 | Schulze | |
| 5,466,243 A | 11/1995 | Schmieding | |
| 5,467,911 A | 11/1995 | Tsuruta | |
| 5,474,566 A | 12/1995 | Alesi | |
| 5,474,567 A | 12/1995 | Stefanchik | |
| 5,522,844 A | 6/1996 | Johnson | |
| 5,527,319 A | 6/1996 | Green | |
| 5,553,765 A | 9/1996 | Knodel | |
| 5,562,685 A | 10/1996 | Mollenauer | |
| 5,564,615 A | 10/1996 | Bishop | |
| 5,582,615 A | 12/1996 | Foshee | |
| 5,582,616 A | 12/1996 | Bolduc | |
| 5,584,425 A | 12/1996 | Savage | |
| 5,588,581 A | 12/1996 | Conlon | |
| 5,601,571 A | 2/1997 | Moss | |
| 5,601,573 A | 2/1997 | Fogelberg | |
| 5,626,613 A | 5/1997 | Schmieding | |
| 5,628,752 A | 5/1997 | Asnis | |
| 5,649,931 A | 7/1997 | Bryant | |
| 5,662,662 A | 9/1997 | Bishop | |
| 5,681,330 A | 10/1997 | Hughett | |
| 5,683,401 A | 11/1997 | Schmieding | |
| 5,685,474 A | 11/1997 | Seeber | |
| 5,697,935 A | 12/1997 | Moran | |
| 5,709,692 A | 1/1998 | Mollenauer | |
| 5,728,116 A | 3/1998 | Rosenman | |
| 5,730,744 A | 3/1998 | Justin et al. | |
| 5,732,806 A | 3/1998 | Foshee | |
| 5,735,854 A | 4/1998 | Caron | |
| 5,741,268 A | 4/1998 | Schutz | |
| 5,762,255 A | 6/1998 | Chrisman | |
| 5,782,844 A * | 7/1998 | Yoon | A61B 17/064 606/139 |
| 5,810,882 A | 9/1998 | Bolduc | |
| 5,824,008 A | 10/1998 | Bolduc | |
| 5,830,221 A | 11/1998 | Stein et al. | |
| 5,843,087 A | 12/1998 | Jensen | |
| 5,897,564 A | 4/1999 | Schulze | |
| 5,904,693 A | 5/1999 | Dicesare | |
| 5,910,105 A | 6/1999 | Swain | |
| 5,911,722 A | 6/1999 | Adler | |
| 5,928,244 A | 7/1999 | Tovey | |
| 5,928,252 A | 7/1999 | Steadman | |
| 5,931,844 A | 8/1999 | Thompson | |
| 5,932,035 A * | 8/1999 | Koger | A61B 8/12 148/563 |
| 5,941,439 A | 8/1999 | Kammerer | |
| 5,954,259 A | 9/1999 | Viola | |
| 5,961,524 A | 10/1999 | Crombie | |
| 5,964,772 A | 10/1999 | Bolduc | |
| 5,976,160 A | 11/1999 | Crainich | |
| 5,997,552 A | 12/1999 | Person | |
| 6,010,513 A | 1/2000 | Tormala | |
| 6,013,991 A | 1/2000 | Philipp | |
| 6,039,753 A | 3/2000 | Meislin | |
| 6,074,395 A | 6/2000 | Trot | |
| 6,099,537 A | 8/2000 | Sugai | |
| 6,126,670 A | 10/2000 | Walker | |
| 6,132,435 A | 10/2000 | Young | |
| 6,146,387 A | 11/2000 | Trot | |
| 6,183,479 B1 | 2/2001 | Tormala | |
| 6,228,098 B1 | 5/2001 | Kayan | |
| 6,235,058 B1 | 5/2001 | Huene | |
| 6,241,736 B1 | 6/2001 | Sater | |
| 6,261,302 B1 * | 7/2001 | Voegele | A61B 90/39 606/142 |
| 6,296,656 B1 | 10/2001 | Bolduc et al. | |
| 6,330,964 B1 | 12/2001 | Kayan | |
| 6,387,113 B1 | 5/2002 | Hawkins | |
| 6,402,757 B1 | 6/2002 | Moore, III | |
| 6,419,644 B1 | 7/2002 | White | |
| 6,425,900 B1 | 7/2002 | Knodel | |
| 6,439,446 B1 | 8/2002 | Perry | |
| 6,440,136 B1 | 8/2002 | Gambale | |
| 6,450,391 B1 | 9/2002 | Kayan | |
| 6,457,625 B1 | 10/2002 | Tormala | |
| 6,551,333 B2 | 4/2003 | Kuhns | |
| 6,562,051 B1 | 5/2003 | Bolduc | |
| 6,572,626 B1 | 6/2003 | Knodel | |
| 6,589,249 B2 | 7/2003 | Sater | |
| 6,592,593 B1 | 7/2003 | Parodi et al. | |
| 6,626,916 B1 | 9/2003 | Yeung | |
| 6,632,228 B2 | 10/2003 | Fortier | |
| 6,652,538 B2 | 11/2003 | Kayan | |
| 6,663,656 B2 | 12/2003 | Schmieding | |
| 6,666,854 B1 * | 12/2003 | Lange | A61B 17/2909 606/1 |
| 6,695,867 B2 | 2/2004 | Ginn | |
| 6,733,506 B1 | 5/2004 | McDevitt | |
| 6,743,240 B2 | 6/2004 | Smith | |
| 6,749,621 B2 | 6/2004 | Pantages | |
| 6,755,836 B1 | 6/2004 | Lewis | |
| 6,773,438 B1 | 8/2004 | Knodel | |
| 6,800,081 B2 | 10/2004 | Parodi | |
| 6,811,552 B2 | 11/2004 | Well, Sr. et al. | |
| 6,824,548 B2 | 11/2004 | Smith | |
| 6,837,893 B2 | 1/2005 | Miller | |
| 6,840,943 B2 | 1/2005 | Kennefick | |
| 6,843,794 B2 | 1/2005 | Sixto | |
| 6,869,435 B2 | 3/2005 | Blake, III | |
| 6,884,248 B2 | 4/2005 | Bolduc | |
| 6,887,244 B1 | 5/2005 | Walker | |
| 6,893,446 B2 | 5/2005 | Sater | |
| 6,905,057 B2 | 6/2005 | Swayze | |
| 6,929,661 B2 | 8/2005 | Bolduc et al. | |
| 6,942,674 B2 | 9/2005 | Belef | |
| 6,945,979 B2 | 9/2005 | Kortenbach | |
| 6,960,217 B2 | 11/2005 | Bolduc | |
| 6,966,919 B2 | 11/2005 | Sixto, Jr. | |
| 6,988,650 B2 | 1/2006 | Schwemberger | |
| 7,000,819 B2 | 2/2006 | Swayze | |
| 7,128,754 B2 | 10/2006 | Bolduc | |
| 7,147,657 B2 | 12/2006 | Chiang et al. | |
| 7,204,847 B1 | 4/2007 | Gambale | |
| 7,261,716 B2 | 8/2007 | Strobel | |
| 7,491,232 B2 | 2/2009 | Bolduc et al. | |
| 7,544,198 B2 | 6/2009 | Parodi | |
| 7,591,842 B2 | 9/2009 | Parodi | |

(56) References Cited

U.S. PATENT DOCUMENTS

| | | |
|---|---|---|
| 7,637,932 B2 | 12/2009 | Bolduc et al. |
| 7,670,362 B2 | 3/2010 | Zergiebel |
| 7,758,612 B2 | 7/2010 | Ship |
| 7,823,267 B2 | 11/2010 | Bolduc |
| 7,828,838 B2 | 11/2010 | Bolduc et al. |
| 7,862,573 B2 | 1/2011 | Darois |
| 7,867,252 B2 | 1/2011 | Criscuolo |
| 7,905,890 B2 | 3/2011 | Whitfield et al. |
| 7,931,660 B2 | 4/2011 | Aranyi et al. |
| 7,959,663 B2 | 6/2011 | Bolduc |
| 7,959,670 B2 | 6/2011 | Bolduc |
| 8,002,811 B2 | 8/2011 | Corradi |
| 8,034,076 B2 | 10/2011 | Criscuolo |
| 8,061,577 B2 * | 11/2011 | Racenet ............ A61B 17/07207 227/175.1 |
| 8,075,570 B2 | 12/2011 | Bolduc et al. |
| 8,083,752 B2 | 12/2011 | Bolduc |
| 8,087,142 B2 * | 1/2012 | Levin .................... A61B 17/064 227/175.1 |
| 8,092,519 B2 | 1/2012 | Bolduc |
| 8,114,099 B2 | 2/2012 | Ship |
| 8,114,101 B2 | 2/2012 | Criscuolo |
| 8,216,272 B2 | 7/2012 | Ship |
| 8,231,639 B2 | 7/2012 | Bolduc et al. |
| 8,282,670 B2 | 10/2012 | Shipp |
| 8,292,933 B2 | 10/2012 | Zergiebel |
| 8,323,314 B2 | 12/2012 | Blier |
| 8,328,823 B2 | 12/2012 | Aranyi et al. |
| 8,343,176 B2 | 1/2013 | Criscuolo |
| 8,343,184 B2 | 1/2013 | Blier |
| 8,382,778 B2 | 2/2013 | Criscuolo |
| 8,414,627 B2 | 4/2013 | Corradi |
| 8,465,520 B2 | 6/2013 | Blier |
| 8,474,679 B2 | 7/2013 | Felix |
| 8,475,453 B2 * | 7/2013 | Marczyk ............ A61B 18/1445 606/51 |
| 8,579,919 B2 | 11/2013 | Bolduc |
| 8,579,920 B2 | 11/2013 | Nering |
| 8,597,311 B2 | 12/2013 | Criscuolo et al. |
| 8,685,044 B2 | 4/2014 | Bolduc et al. |
| 8,690,897 B2 | 4/2014 | Bolduc |
| 8,728,102 B2 | 5/2014 | Criscuolo et al. |
| 8,728,120 B2 | 5/2014 | Blier |
| 8,777,969 B2 | 7/2014 | Kayan |
| 8,821,514 B2 | 9/2014 | Aranyi |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 8,920,439 B2 | 12/2014 | Cardinale et al. |
| 8,926,637 B2 | 1/2015 | Zergiebel |
| 8,968,311 B2 | 3/2015 | Allen, IV et al. |
| 9,017,345 B2 | 4/2015 | Taylor et al. |
| 9,023,065 B2 | 5/2015 | Bolduc et al. |
| 9,028,495 B2 | 5/2015 | Mueller et al. |
| 9,186,138 B2 | 11/2015 | Corradi et al. |
| 9,259,221 B2 | 2/2016 | Zergiebel |
| 9,282,961 B2 | 3/2016 | Whitman et al. |
| 9,332,983 B2 | 5/2016 | Shipp |
| 9,351,728 B2 | 5/2016 | Sniffin et al. |
| 9,351,733 B2 | 5/2016 | Fischvogt |
| 9,358,004 B2 | 6/2016 | Sniffin et al. |
| 9,358,010 B2 | 6/2016 | Wenchell et al. |
| 9,364,274 B2 | 6/2016 | Zergiebel |
| 9,402,623 B2 | 8/2016 | Kayan |
| 9,486,218 B2 | 11/2016 | Criscuolo et al. |
| 9,526,498 B2 | 12/2016 | Reed |
| 9,655,621 B2 | 5/2017 | Abuzaina et al. |
| 9,662,106 B2 | 5/2017 | Corradi et al. |
| 9,668,730 B2 | 6/2017 | Sniffin et al. |
| 2003/0009441 A1 * | 1/2003 | Holsten ................ A61B 17/068 |
| 2003/0114839 A1 | 6/2003 | Looper et al. |
| 2004/0092937 A1 | 5/2004 | Criscuolo |
| 2004/0111089 A1 | 6/2004 | Stevens et al. |
| 2004/0127916 A1 | 7/2004 | Bolduc et al. |
| 2004/0181222 A1 | 9/2004 | Culbert et al. |
| 2004/0193217 A1 | 9/2004 | Lubbers et al. |
| 2004/0204723 A1 | 10/2004 | Kayan |
| 2004/0243139 A1 | 12/2004 | Lewis et al. |
| 2006/0100629 A1 | 5/2006 | Lee |
| 2006/0129152 A1 | 6/2006 | Ship |
| 2007/0038220 A1 | 2/2007 | Ship |
| 2007/0088390 A1 | 4/2007 | Paz et al. |
| 2007/0162030 A1 | 7/2007 | Aranyi |
| 2008/0097523 A1 | 4/2008 | Bolduc |
| 2008/0147113 A1 * | 6/2008 | Nobis .................... A61B 17/29 606/205 |
| 2008/0188868 A1 | 8/2008 | Weitzner et al. |
| 2008/0243106 A1 | 10/2008 | Coe et al. |
| 2008/0281336 A1 | 11/2008 | Zergiebel |
| 2008/0312687 A1 | 12/2008 | Blier |
| 2009/0112234 A1 | 4/2009 | Crainich et al. |
| 2009/0118776 A1 | 5/2009 | Kelsch |
| 2009/0188965 A1 * | 7/2009 | Levin .................... A61B 17/064 227/179.1 |
| 2010/0030262 A1 | 2/2010 | McLean et al. |
| 2010/0094083 A1 * | 4/2010 | Taylor .................... A61B 17/04 600/106 |
| 2010/0270354 A1 | 10/2010 | Rimer |
| 2010/0292710 A1 | 11/2010 | Daniel |
| 2010/0292713 A1 | 11/2010 | Cohn |
| 2010/0292715 A1 | 11/2010 | Nering |
| 2011/0022065 A1 | 1/2011 | Shipp |
| 2011/0042441 A1 | 2/2011 | Shelton, IV et al. |
| 2011/0060349 A1 | 3/2011 | Cheng et al. |
| 2011/0071578 A1 * | 3/2011 | Colesanti ............. A61B 17/064 606/305 |
| 2011/0079627 A1 | 4/2011 | Cardinale |
| 2011/0087240 A1 | 4/2011 | Shipp |
| 2011/0121049 A1 | 5/2011 | Malinouskas |
| 2011/0204120 A1 | 8/2011 | Crainich |
| 2011/0276057 A1 * | 11/2011 | Conlon .................. A61B 17/29 606/130 |
| 2011/0295269 A1 | 12/2011 | Swensgard et al. |
| 2011/0295282 A1 | 12/2011 | Glick |
| 2012/0022554 A1 | 1/2012 | Paik |
| 2012/0059397 A1 | 3/2012 | Criscuolo et al. |
| 2012/0083770 A1 | 4/2012 | Paik |
| 2012/0109157 A1 | 5/2012 | Criscuolo et al. |
| 2013/0018392 A1 | 1/2013 | Zergiebel |
| 2013/0098966 A1 | 4/2013 | Kostrzewski |
| 2013/0110088 A1 | 5/2013 | Wenchell |
| 2013/0131700 A1 | 5/2013 | Criscuolo |
| 2013/0197591 A1 | 8/2013 | Corradi |
| 2014/0114329 A1 | 4/2014 | Zergiebel |
| 2014/0121684 A1 | 5/2014 | Criscuolo |
| 2014/0200587 A1 | 7/2014 | Pompee et al. |
| 2014/0243855 A1 | 8/2014 | Sholev et al. |
| 2014/0276967 A1 | 9/2014 | Fischvogt et al. |
| 2014/0276969 A1 | 9/2014 | Wenchell et al. |
| 2014/0276972 A1 | 9/2014 | Abuzaina et al. |
| 2014/0316446 A1 | 10/2014 | Kayan |
| 2014/0371765 A1 | 12/2014 | Corradi et al. |
| 2015/0001272 A1 | 1/2015 | Sniffin et al. |
| 2015/0005748 A1 | 1/2015 | Sniffin et al. |
| 2015/0005788 A1 | 1/2015 | Sniffin et al. |
| 2015/0005789 A1 | 1/2015 | Sniffin et al. |
| 2015/0018847 A1 | 1/2015 | Criscuolo et al. |
| 2015/0032130 A1 | 1/2015 | Russo |
| 2015/0080888 A1 * | 3/2015 | Mueller ................ A61B 17/29 606/41 |
| 2015/0080911 A1 | 3/2015 | Reed |
| 2015/0133970 A1 | 5/2015 | Ranucci et al. |
| 2015/0133971 A1 | 5/2015 | Ranucci et al. |
| 2015/0133972 A1 | 5/2015 | Ranucci et al. |
| 2015/0150558 A1 | 6/2015 | Zergiebel |
| 2015/0209043 A1 * | 7/2015 | Taylor .................. A61B 17/068 606/139 |
| 2015/0327859 A1 | 11/2015 | Bolduc |
| 2016/0007991 A1 | 1/2016 | Bolduc |
| 2016/0007996 A1 | 1/2016 | Bolduc |
| 2016/0066971 A1 | 3/2016 | Corradi et al. |
| 2016/0074034 A1 | 3/2016 | Shipp |
| 2016/0135807 A1 | 5/2016 | Zergiebel |

(56) References Cited

U.S. PATENT DOCUMENTS

| | | | |
|---|---|---|---|
| 2016/0166255 A1* | 6/2016 | Fischvogt | A61B 17/064 606/139 |
| 2016/0249912 A1 | 9/2016 | Fischvogt | |
| 2016/0270778 A1 | 9/2016 | Zergiebel | |
| 2016/0270835 A1 | 9/2016 | Reed | |
| 2016/0278766 A1 | 9/2016 | Wenchell et al. | |
| 2016/0338694 A1 | 11/2016 | Kayan | |
| 2016/0345967 A1 | 12/2016 | Sniffin et al. | |
| 2017/0042657 A1 | 2/2017 | Criscuolo et al. | |
| 2017/0128068 A1 | 5/2017 | Zhang et al. | |
| 2017/0151048 A1 | 6/2017 | Russo | |

FOREIGN PATENT DOCUMENTS

| | | |
|---|---|---|
| EP | 0 374 088 | 6/1990 |
| EP | 0 834 280 | 4/1998 |
| EP | 1 273 272 | 1/2003 |
| EP | 1990013 A1 | 11/2008 |
| EP | 2 055 241 A2 | 5/2009 |
| EP | 1908409 B1 | 12/2010 |
| EP | 2399538 A2 | 12/2011 |
| EP | 2484294 A1 | 8/2012 |
| EP | 2853202 A2 | 4/2015 |
| JP | 9149906 | 6/1997 |
| WO | 00/16701 A1 | 3/2000 |
| WO | WO 2002/034140 | 5/2002 |
| WO | WO 2003/034925 | 5/2003 |
| WO | WO 2003/103507 | 12/2003 |
| WO | WO 2004/112841 | 12/2004 |
| WO | 2005004727 A1 | 1/2005 |
| WO | WO 2009/039506 | 3/2009 |
| WO | 2012/064692 A2 | 5/2012 |
| WO | 2013/046115 A1 | 4/2013 |

OTHER PUBLICATIONS

Extended European Search Report corresponding to EP No. 10 01 2659.8, completed Dec. 21, 2010 and dated Jan. 3, 2011; 3 pages.
Extended European Search Report corresponding to EP No. 10 01 2646.5, completed Feb. 11, 2011 and dated Feb. 22, 2011; 3 pages.
Extended European Search Report corresponding to EP No. 11 25 0549.0, completed Sep. 9, 2013 and dated Sep. 17, 2014; 9 pages.
Extended European Search Report corresponding to EP 14 15 9394.7, completed Apr. 16, 2014 and dated Apr. 29, 2014; (8 pp).
Extended European Search Report corresponding to EP 14 15 8946.5, completed Jun. 20, 2014 and dated Jul. 8, 2014; (9 pp).
Extended European Search Report corresponding to EP 14 17 8107.0, completed Nov. 24, 2014 and dated Dec. 3, 2014; (5 pp).
Extended European Search Report corresponding to EP 14 17 4656.0, completed Jan. 16, 2015 and dated Jan. 26, 2015; (7 pp).
Extended European Search Report corresponding to EP 14 18 4907.5, completed Jan. 12, 2015 and dated Jan. 27, 2015; (9 pp).
Extended European Search Report corresponding to counterpart application EP 14 19 7885.8 dated Apr. 30, 2015; 9pp.
Extended European Search Report corresponding to counterpart application EP 14 18 1900.3 dated Apr. 9, 2015; 7pp.
Extended European Search Report corresponding to Int'l Application No. EP 14 15 1663.3 dated Jun. 7, 2016.
Chinese First Office Action corresponding to counterpart Int'l Appln. No. CN 2014100975478 dated Mar. 22, 2017.
Extended European Search Report corresponding to counterpart Int'l Appln. No. EP 14 81 7036.8 dated Feb. 2, 2017.
European Office Action corresponding to counterpart Int'l Appln. No. EP 14 19 7885.8 dated Feb. 7, 2017.
Chinese First Office Action corresponding to counterpart Int'l Appln. No. CN 201410090675 dated Feb. 28, 2017.
Extended European Search Report corresponding to counterpart Int'l Appln. No. EP 16 19 8333.3 dated Mar. 15, 2017.
European Office Action corresponding to counterpart Int'l Appln. No. EP 14 15 16633 dated May 10, 2017.
Extended European Search Report corresponding to counterpart Int'l Appln. No. EP 17 15 7259.7 dated May 10, 2017.
Chinese First Office Action corresponding to counterpart Int'l Appln. No. CN 2014103559671 dated Jun. 13, 2017.
Australian Examination Report No. 1 corresponding to counterpart Int'l Appln. No. AU 2014200071 dated Jun. 20, 2017.
Australian Examination Report No. 1 corresponding to counterpart Int'l Appln. No. AU 2014201338 dated Jul. 10, 2017.

* cited by examiner

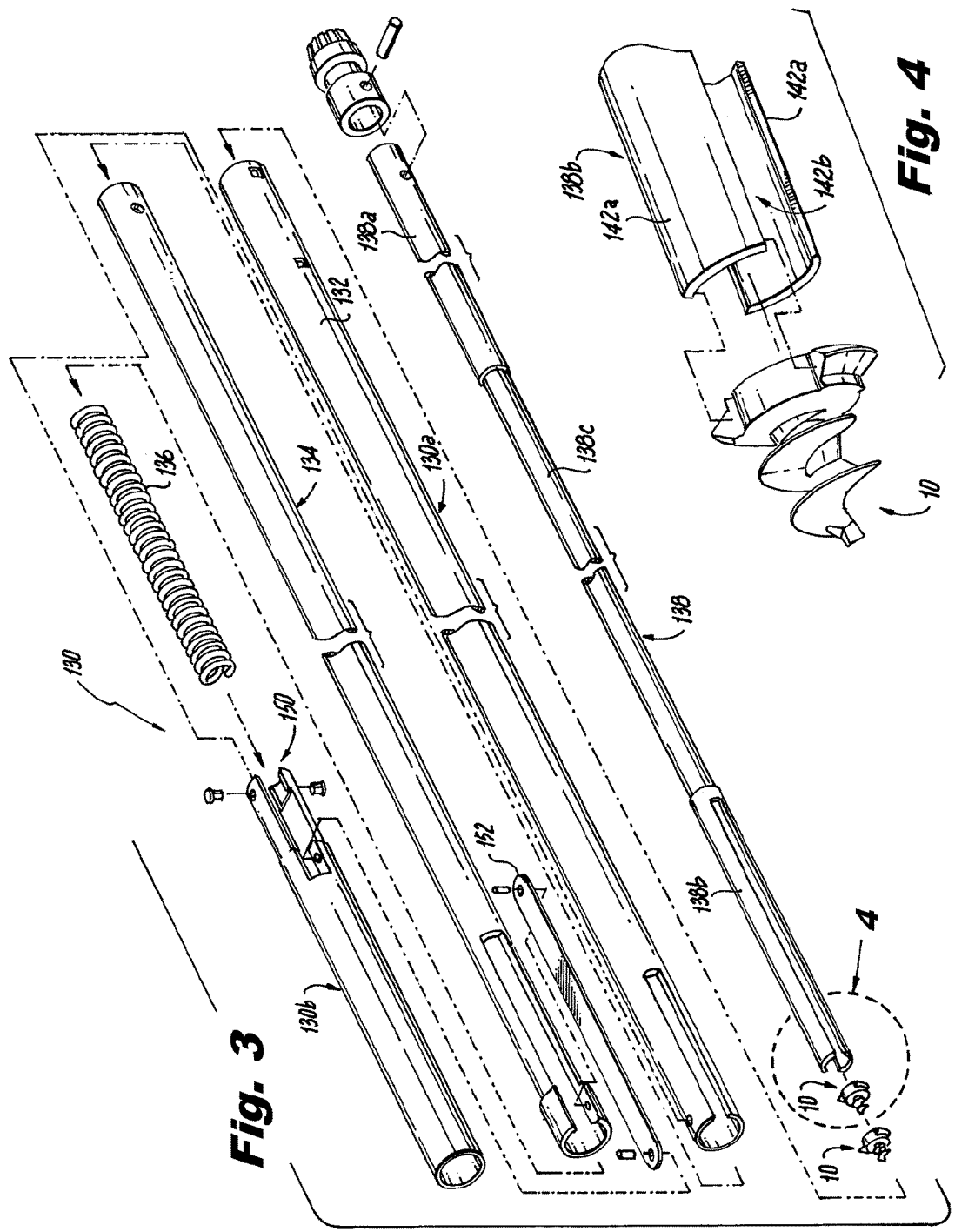

ARTICULATION JOINT FOR APPARATUS FOR ENDOSCOPIC PROCEDURES

CROSS-REFERENCE TO RELATED APPLICATIONS

This application claims the benefit of and priority to U.S. Provisional Patent Application No. 61/783,559, filed Mar. 14, 2013, the entire disclosure of which is incorporated by reference herein.

BACKGROUND

1. Technical Field

The present disclosure relates to surgical apparatus, devices and/or systems for performing endoscopic surgical procedures and methods of use thereof. More specifically, the present disclosure relates to an articulation joint for surgical apparatus, devices and/or systems for performing endoscopic surgical procedures.

2. Background of Related Art

During laparoscopic or endoscopic surgical procedures, access to a surgical site is achieved through a small incision or through a narrow cannula inserted through a small entrance wound in a patient. Because of limited area to access the surgical site, many endoscopic surgical devices include mechanisms for articulating the tool assembly of the device. Typically, the articulating mechanism is controlled by an actuator which has to be manipulated by a surgeon to properly orient the tool assembly in relation to tissue to be treated.

Some endoscopic surgical devices utilize torque-transmitting flexible drive cables and the like to transmit rotation around an articulation joint of the endoscopic surgical device. In order to accommodate the articulation desired, relatively more flexible torque-transmitting cables are used. However, the more flexible a cable is, the more "wind-up" of the cable that takes place and the more loss of the torque transmission that occurs.

Accordingly, a need exists for endoscopic surgical devices which utilize torque-transmitting flexible drive cables capable of transmitting relatively more torque, with a decrease in the degree of loss of torque transmission while maintaining a degree of articulation of the endoscopic surgical device.

SUMMARY

The present disclosure relates to electromechanical, hand-held surgical apparatus, devices and/or systems configured for use with removable disposable loading units and/or single use loading units for clamping, cutting and/or stapling tissue.

According to an aspect of the present disclosure, an endoscopic surgical device is provided and includes a handle assembly including a handle housing and a trigger operatively connected to the handle housing, and a drive mechanism actuatable by the trigger; and an endoscopic anchor retaining/advancing assembly extending from the handle assembly. The endoscopic anchor retaining/advancing assembly including a proximal tube portion and a distal tube portion pivotably connected to one another at an articulation joint, each of the proximal tube portion and the distal tube portion defining a central longitudinal axis; a proximal inner shaft rotatably disposed within the proximal tube portion, wherein the proximal inner shaft is relatively rigid, and wherein the proximal inner shaft is mechanically connected to the drive mechanism such that actuation of the trigger results in rotation of the proximal inner shaft; a distal inner shaft rotatably disposed within the distal tube portion, wherein the distal inner shaft is relatively rigid; and an intermediate drive cable mechanically interconnecting the proximal inner shaft and the distal inner shaft, wherein the intermediate drive cable is relatively flexible as compared to the proximal inner shaft and the distal inner shaft, wherein the intermediate drive cable extends from and between the proximal tube portion and the distal tube portion, across the articulation joint, wherein the intermediate drive cable defines a central longitudinal axis and wherein the central longitudinal axis of the intermediate drive cable is off-set a radial distance from the central longitudinal axis of the proximal tube portion and the distal tube portion.

The endoscopic surgical device also including at least one fastener loaded in the distal tube portion, wherein the at least one fastener is acted upon by the distal inner shaft upon an actuation of the trigger.

According to another aspect of the present disclosure, an endoscopic surgical device is provided which comprises an endoscopic anchor retaining/advancing assembly including a proximal tube portion and a distal tube portion pivotably connected to one another at an articulation joint, each of the proximal tube portion and the distal tube portion defining a central longitudinal axis; a proximal inner shaft rotatably disposed within the proximal tube portion, wherein the proximal inner shaft is relatively rigid, and wherein the proximal inner shaft is mechanically connected to a drive mechanism such that actuation of the drive mechanism results in rotation of the proximal inner shaft; a distal inner shaft rotatably disposed within the distal tube portion, wherein the distal inner shaft is relatively rigid; and an intermediate drive cable mechanically interconnecting the proximal inner shaft and the distal inner shaft, wherein the intermediate drive cable is relatively flexible as compared to the proximal inner shaft and the distal inner shaft, wherein the intermediate drive cable extends from and between the proximal tube portion and the distal tube portion, across the articulation joint, wherein the intermediate drive cable defines a central longitudinal axis and wherein the central longitudinal axis of the intermediate drive cable is off-set a radial distance from the central longitudinal axis of the proximal tube portion and the distal tube portion.

The endoscopic surgical device also comprises at least one fastener loaded in the distal tube portion, wherein the at least one fastener is acted upon by the distal inner shaft upon an actuation of the drive mechanism.

The distal tube portion may be is articulatable between a non-articulated orientation and a plurality of articulated orientations relative to the proximal tube portion.

The central longitudinal axis of the proximal tube portion and the central longitudinal axis of the distal tube portion may define a central radius of curvature for each articulated orientation of the distal tube portion relative to the proximal tube portion. The central longitudinal axis of the intermediate drive cable may define a radius of curvature that is greater than the central radius of curvature for each articulated orientation of the distal tube portion relative to the proximal tube portion.

The central longitudinal axis of the intermediate drive cable may be off-set from the central longitudinal axis of the proximal tube portion and the central longitudinal axis of the distal tube portion in a direction away from a direction of articulation of the distal tube portion relative to the proximal tube portion.

The intermediate drive cable may have an outer diameter of about 0.08" and wherein the proximal tube portion and the distal tube portion may each have an outer diameter of about 0.22".

A ratio of an outer diameter of the intermediate flexible drive cable to an outer diameter of either the proximal tube portion or the distal tube portion may be 2.8.

Further details and aspects of exemplary embodiments of the present invention are described in more detail below with reference to the appended figures.

BRIEF DESCRIPTION OF THE DRAWINGS

Embodiments of the present disclosure are described herein with reference to the accompanying drawings, wherein:

FIG. 3 is an enlarged, perspective view, with parts separated, of an endoscopic anchor retaining/advancing assembly of the endoscopic surgical device of FIGS. 1 and 2;

FIG. 4 is an enlarged view of the indicated area of detail of FIG. 3;

DETAILED DESCRIPTION OF EMBODIMENTS

Figure 1:
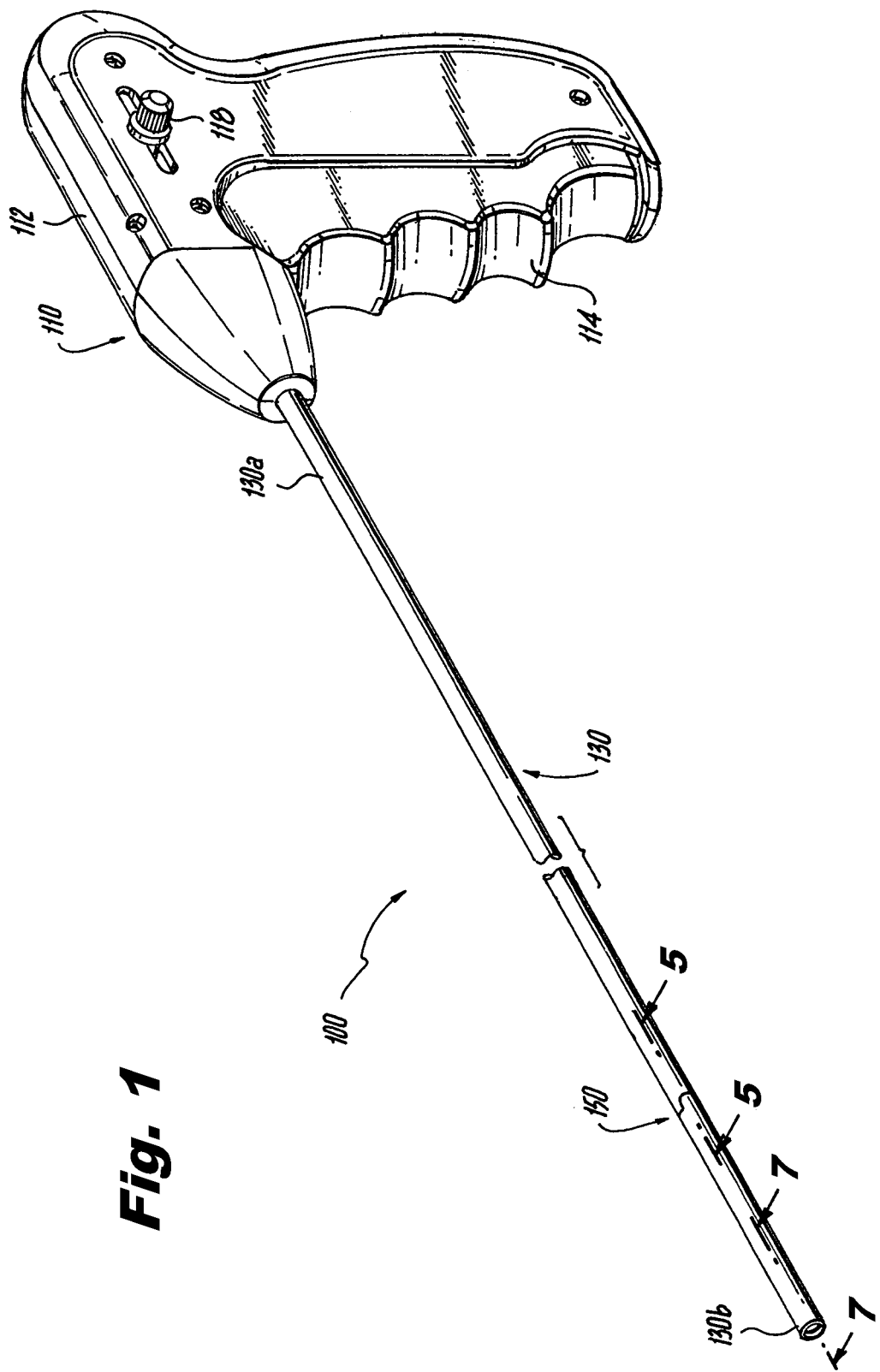
FIG. 1 is a perspective view of an endoscopic surgical device according to an aspect of the present disclosure.

Embodiments of the presently disclosed endoscopic surgical device is described in detail with reference to the drawings, in which like reference numerals designate identical or corresponding elements in each of the several views. As used herein the term "distal" refers to that portion of the endoscopic surgical device, that is farther from the user, while the term "proximal" refers to that portion of the endoscopic surgical device that is closer to the user.

Non-limiting examples of endoscopic surgical devices which may include articulation joints according to the present disclosure include manual, mechanical and/or electromechanical surgical tack appliers, surgical clip appliers, surgical staplers, surgical stitching devices and the like.

Referring initially to FIGS. 1-7, an exemplary endoscopic surgical device, in the form of an endoscopic surgical tack applier is shown generally as 100. Tack applier 100 includes a handle assembly 110, and an endoscopic anchor retaining/advancing assembly 130 extending from handle assembly 110 and configured to store and selectively release or fire a plurality of anchors 10 therefrom.

In accordance with the present disclosure, it is contemplated that endoscopic anchor retaining/advancing assembly 130 may include a pivot or articulation joint 150 provided along a length thereof. As seen in FIGS. 1-6, endoscopic anchor retaining/advancing assembly 130 includes a proximal tube portion 130a, a distal tube portion 130b pivotally connected to proximal tube portion 130a by a pivot pin 130c at articulation joint 150.

Figure 2:
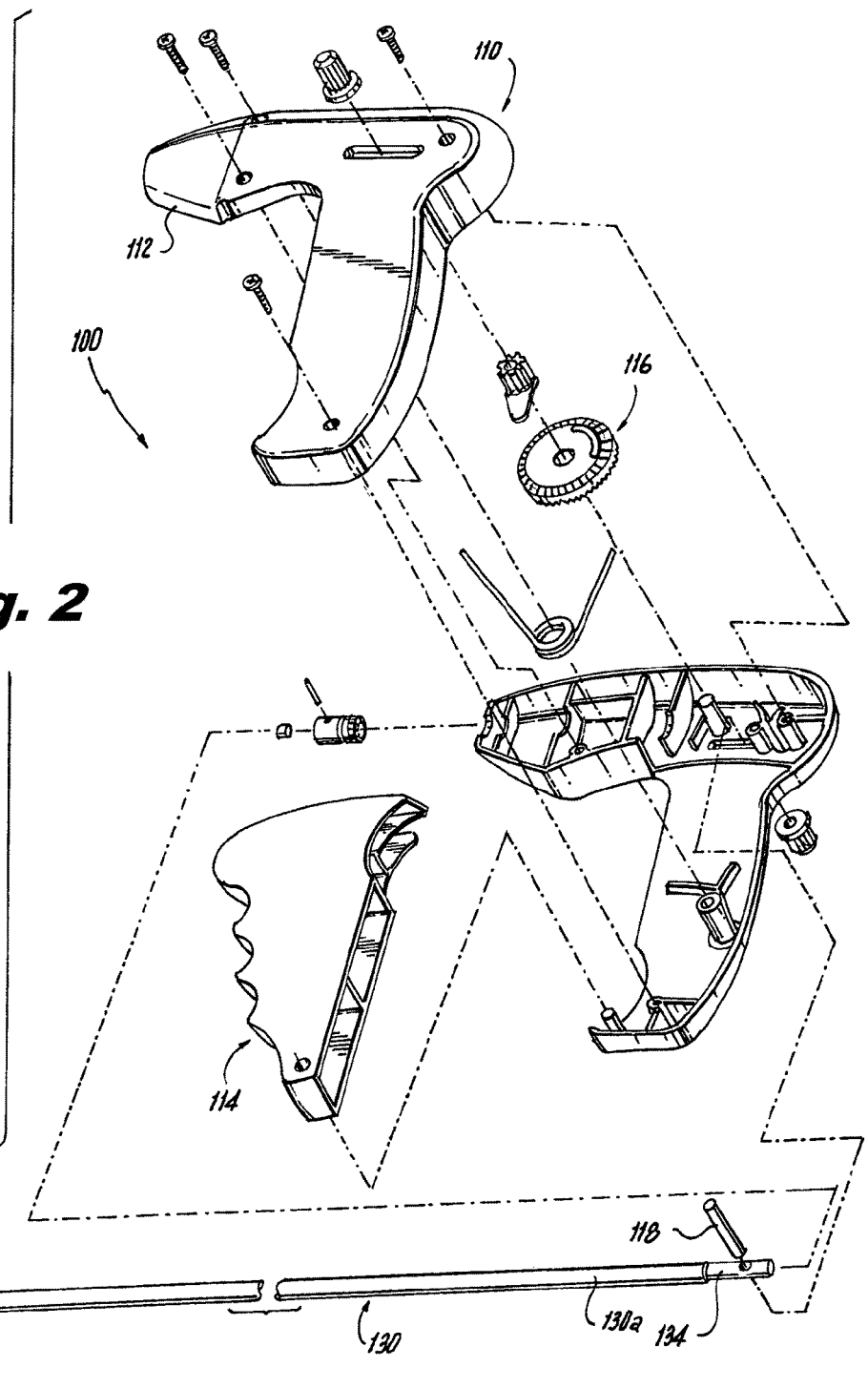
FIG. 2 is a perspective view, with parts separated, of the endoscopic surgical device of FIG. 1.

As seen in FIGS. 1 and 2, handle assembly 110 includes a handle housing 112 pivotably supporting a trigger 114. Trigger 114 is operatively connected to a drive mechanism 116 such that each squeeze of trigger 114 results in a rotation of an inner shaft assembly 138 of proximal tube portion 130a of anchor retaining/advancing assembly 130.

Reference may be made to U.S. Patent Publication No. 2011/0087240, filed on Oct. 20, 2010, the entire content of which is incorporated herein by reference, for a discussion and description of the operation and construction of aspects of handle assembly 110 and/or anchor retaining/advancing assembly 130 of tack applier 100, and for a discussion and description of the construction of anchors 10.

As seen in FIGS. 1-6, proximal tube portion 130a of anchor retaining/advancing assembly 130 includes an outer proximal tube 132 secured to and extending from handle housing 112, a stiffener tube 134 concentrically and slidably disposed within outer proximal tube 132, and a relatively rigid proximal inner shaft 138a of inner shaft assembly 138 rotatably disposed within stiffener tube 134.

Inner shaft assembly 138 includes a relatively rigid proximal inner shaft 138a, a relatively rigid distal inner shaft 138b, and an intermediate flexible drive cable 138c interconnecting proximal inner shaft 138a and distal inner shaft 138b. Desirably, intermediate flexible drive cable 138c is non-rotatably connected to each of proximal inner shaft 138a and distal inner shaft 138b, and slidably coupled to at least one of proximal inner shaft 138a and distal inner shaft 138b to accommodate and/or account for variations in length of intermediate flexible drive cable 138c when intermediate flexible drive cable 138c is in a flexed condition. It is also desirable that the drive cable 138c is long enough that it extends proximally past the most proximal pivot of the articulation link. This reduces bending stresses on the interface between the drive cable 138c and the proximal inner shaft 138a.

Proximal inner shaft 138a extends into handle housing 112 and is acted upon by drive mechanism 116. A distal end portion of distal inner shaft 138b is slotted, defining a pair of tines 142a and a central channel 142b. The distal end portion of distal inner shaft 138b is configured to retain a plurality of anchors 10 within distal tube portion 130b of anchor retaining/advancing assembly 130.

In particular, anchors 10 are loaded into the distal end portion of distal inner shaft 138b of anchor retaining/advancing assembly 130 such that a pair of opposing threaded sections (not shown) of each anchor 10 extend radially beyond a diameter of distal inner shaft 138b and are slidably disposed within a helical groove of a coil 136 (FIG. 7) defined or provided in distal tube portion 130b of anchor retaining/advancing assembly 130, and the pair of tines 142a of the distal end portion of distal inner shaft 138b are disposed within a pair of slotted sections (not shown) of each anchor 10.

Figure 7:
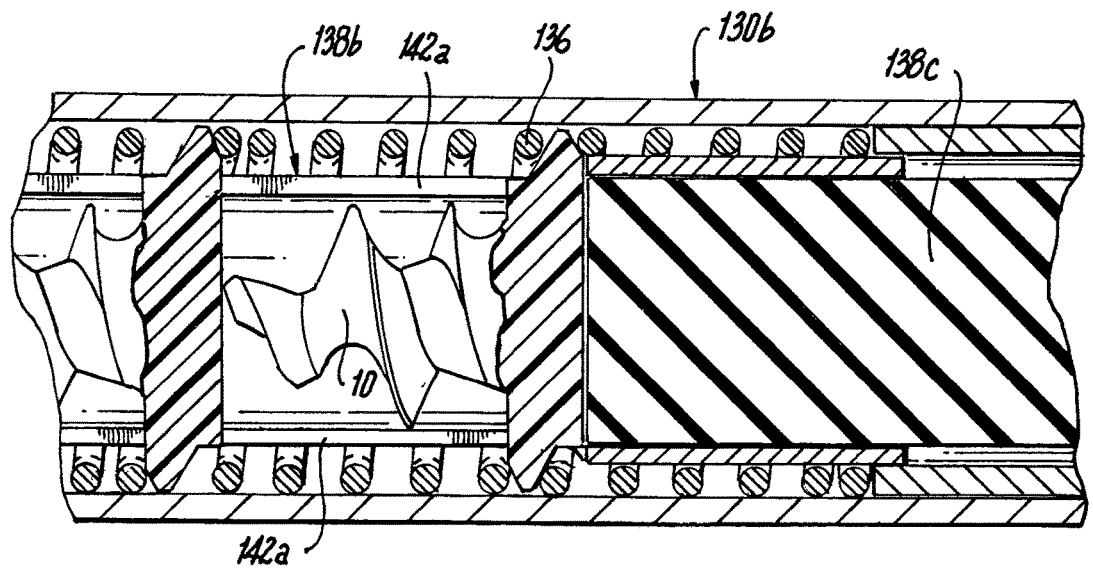
FIG. 7 is an enlarged, cross-sectional view of a distal end of the endoscopic anchor retaining/advancing assembly, as taken along 7-7 of FIG. 1.

As seen in FIGS. 3 and 7, a spiral or coil 136 is fixedly disposed within distal tube portion 130b of anchor retaining/ advancing assembly 130. Distal inner shaft 138*b* extends into and is rotatable within coil 136.

As seen in FIGS. 1-3, 5 and 6, articulation joint 150 includes an articulation link 152 having a proximal end 152*a* and a distal end 152*b*. Proximal end 152*a* of articulation link 152 is pivotally connected to a distal end of stiffener tube 134. Distal end 152*b* of articulation link 150 is pivotally connected to distal tube portion 130*b* of anchor retaining/advancing assembly 130, at a location offset a transverse distance from a central longitudinal axis "X" of proximal tube portion 130*a* of anchor retaining/advancing assembly 130.

In accordance with the present disclosure, an articulation actuation button 118 may be slidably supported on handle housing 112. In use, it is contemplated that articulation actuation button 118 has a distal-most portion wherein distal tube portion 130*b* of anchor retaining/advancing assembly 130 is oriented at about 0° relative to the central longitudinal axis "X", and a proximal-most portion wherein distal tube portion 130*b* of anchor retaining/advancing assembly 130 is oriented at about 90° relative to the central longitudinal axis "X".

Specifically, with articulation actuation button 118 in a distal-most portion, and with distal tube portion 130*b* of anchor retaining/advancing assembly 130 oriented at about 0° relative to the central longitudinal axis "X", as articulation actuation button 118 is moved in a proximal direction, articulation actuation button 118 draws stiffener tube 134 is a proximal direction which draws articulation link 152 in a proximal direction, causing distal tube portion 130*b* of anchor retaining/advancing assembly 130 to pivot about pivot pin 130*c*.

Additionally, with articulation actuation button 118 in a non-distal-most portion, and with distal tube portion 130*b* of anchor retaining/advancing assembly 130 oriented at a non-0° relative to the central longitudinal axis "X", as articulation actuation button 118 is moved in a distal direction, articulation actuation button 118 pushes stiffener tube 134 is a distal direction which pushes articulation link 152 in a distal direction, causing distal tube portion 130*b* of anchor retaining/advancing assembly 130 to pivot about pivot pin 130*c* toward an orientation of 0° relative to the central longitudinal axis "X".

In use, when distal tube portion 130*b* of anchor retaining/advancing assembly 130 is actuated to an off-axis orientation, as will be discussed in greater detail below, distal tube portion 130*b* of anchor retaining/advancing assembly 130 may be angled from between about 0° to about 90° relative to the central longitudinal axis "X".

In accordance with the present disclosure, distal tube portion 130*b* of anchor retaining/advancing assembly 130 is pivotable in a single direction relative to proximal tube portion 130*a* of anchor retaining/advancing assembly 130.

In an alternate embodiment, it is contemplated that handle assembly 110 of tack applier 100 may rotatably support an articulation collar near a proximal end of anchor retaining/advancing assembly 130. It is envisioned that the articulation collar may threadably engage with a threaded end or portion of stiffener tube 134 or some other articulation rod that is pivotably connected to articulation link 152. In this manner, as the articulation collar is rotated, the threads of the articulation collar act on the threads of stiffener tube 134 and cause the stiffener tube 134 to axially translate. As stiffener tube 134 axially translates, said axial translation is transmitted to articulation link 154 to effectuate articulation of distal tube portion 130*b* relative to proximal tube portion 130*a*, as described above.

Figure 5:
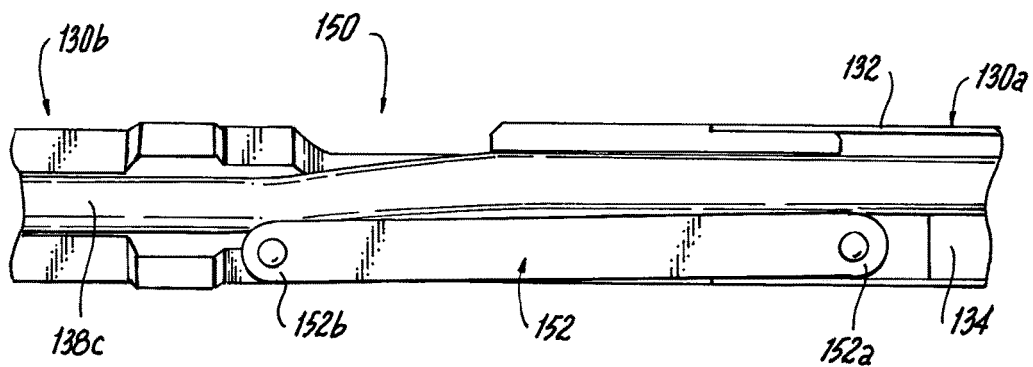
FIG. 5 is a cross-sectional view of an articulation joint of the endoscopic anchor retaining/advancing assembly, as taken through 5-5 of FIG. 1, shown in an non-articulated condition.
Figure 6:
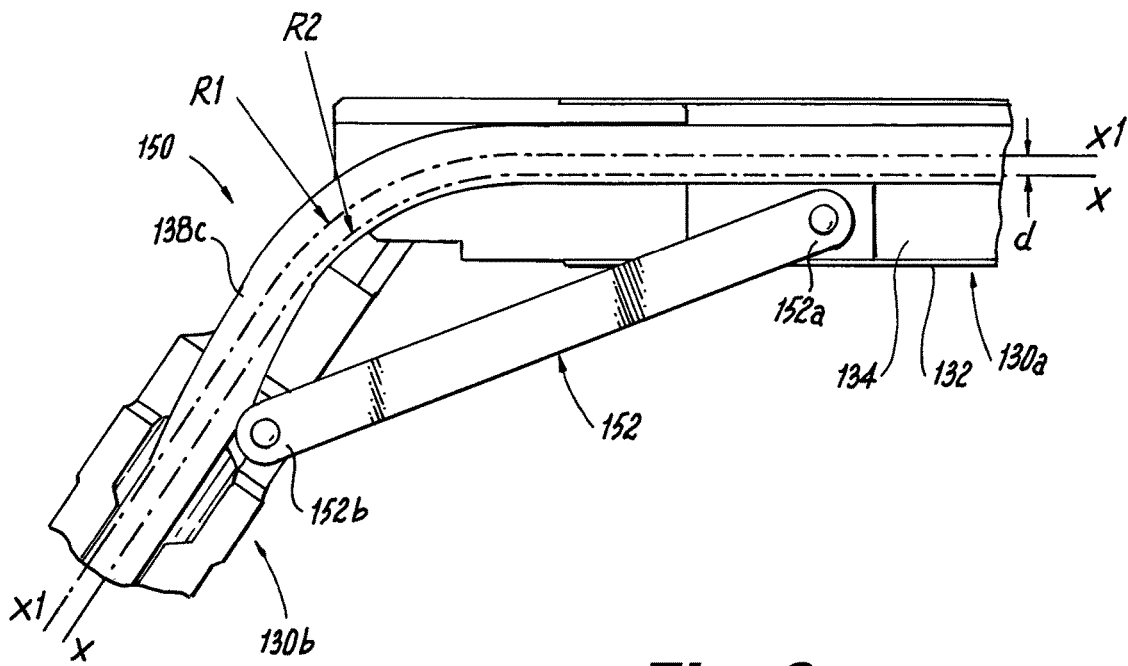
FIG. 6 is a cross-sectional view of an articulation joint of the endoscopic anchor retaining/advancing assembly, as taken through 5-5 of FIG. 1, shown in an articulated condition.

In accordance with the present disclosure, as seen in FIGS. 5 and 6, intermediate flexible drive cable 138*c* extends from proximal tube portion 130*a* to distal tube portion 130*b* of anchor retaining/advancing assembly 130, across articulation joint 150. Intermediate flexible drive cable 138*c* is fabricated from a torsionally stiff and flexible material, such as, for example, stainless steel. Flexible drive cable 138*c* is more flexible as compared to proximal inner shaft 138*a* and distal inner shaft 138*b*.

Intermediate flexible drive cable 138*c* defines a central longitudinal axis "X1" which is off-set a radial distance "r" from the central longitudinal axis "X" of proximal tube portion 130*a* of anchor retaining/advancing assembly 130. The central longitudinal axis "X1" of intermediate flexible drive cable 138*c* is off-set from the central longitudinal axis "X" of proximal tube portion 130*a* of anchor retaining/advancing assembly 130 in a direction away from a direction of articulation of articulation joint 150, or in a direction away from articulation link 152.

As such, as seen in FIG. 6, when distal tube portion 130*b* of anchor retaining/advancing assembly 130 is in an angled orientation, a radius of curvature "R1" of intermediate flexible drive cable 138*c* is relatively greater than a radius of curvature "R2" of a comparable flexible drive cable that would be located along the central longitudinal axis "X" of proximal tube portion 130*a* of anchor retaining/advancing assembly 130.

In this manner, by providing for a larger radius of curvature "R1" for intermediate flexible drive cable 138*c*, it is contemplated, in accordance with the present disclosure, that an intermediate flexible drive cable 138*c* having a relatively larger diameter or constructed from a relatively stiffer material can be used, as compared to any comparable flexible drive cable that would be located along the central longitudinal axis "X" of proximal tube portion 130*a* of anchor retaining/advancing assembly 130.

In so doing, relatively greater torsional forces, and more accurate rotation, can be transmitted along intermediate flexible drive cable 138*c* as compared to any comparable flexible drive cable that would be located along the central longitudinal axis "X" of proximal tube portion 130*a* of anchor retaining/advancing assembly 130.

Intermediate flexible drive cable 138*c* may have an outer diameter of about 0.08". Proximal tube portion 130*a* and distal tube portion 130*b* each have an outer diameter of about 0.22". A ratio of the outer diameter of the intermediate flexible drive cable 138*c* to the outer diameter of either proximal tube portion 130*a* or distal tube portion 130*b* is about 2.8.

Figure 8:
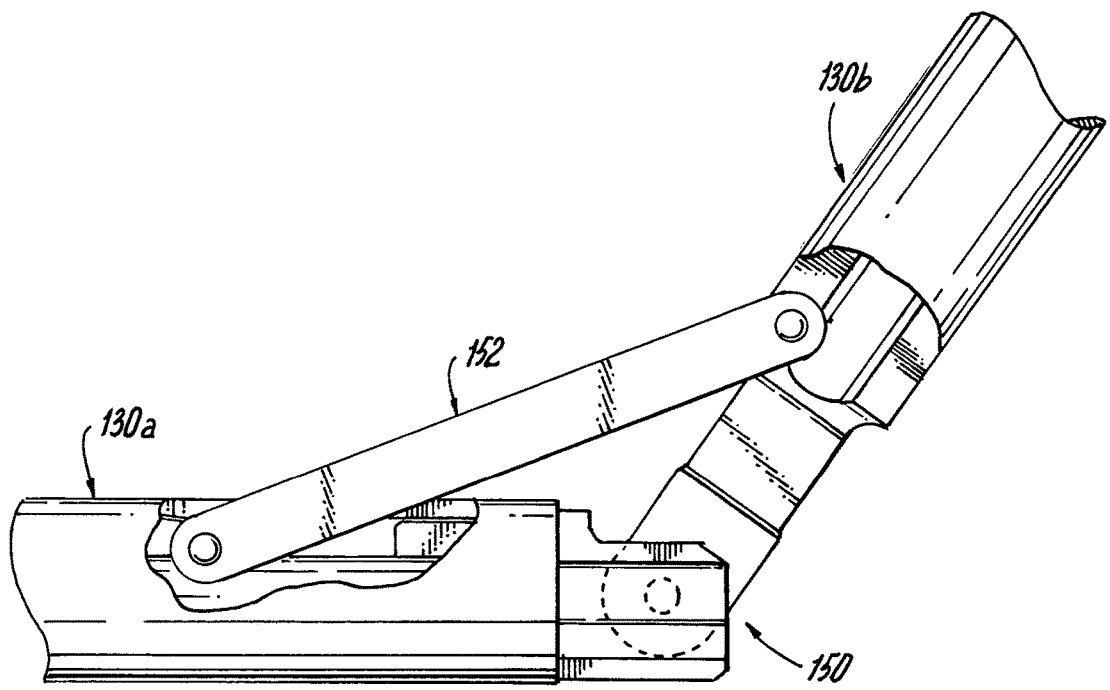
FIG. 8 is a perspective view of an alternate embodiment of a distal end of the endoscopic anchor retaining/advancing assembly for use in an endoscopic surgical device.

In accordance with the present disclosure, as seen in FIG. 8, it is contemplated that tack applier 100 may be configured such that distal tube portion 130*b* of anchor retaining/advancing assembly 130 is configured and adapted to releasably and selectively receive a disposable loading unit (DLU) or single use loading unit (SULU), wherein the DLU or SULU includes at least an outer tube, a coil or helical thread provided along an interior of the outer tube, and an inner shaft rotatably disposed within the coil or helical thread. The inner shaft including a splined distal end portion configured to support at least one anchor 10, and a proximal end portion configured and adapted for mechanical and non-rotational connection to a distal end of an exemplary intermediate flexible drive cable 138*c*.

Figure 9:
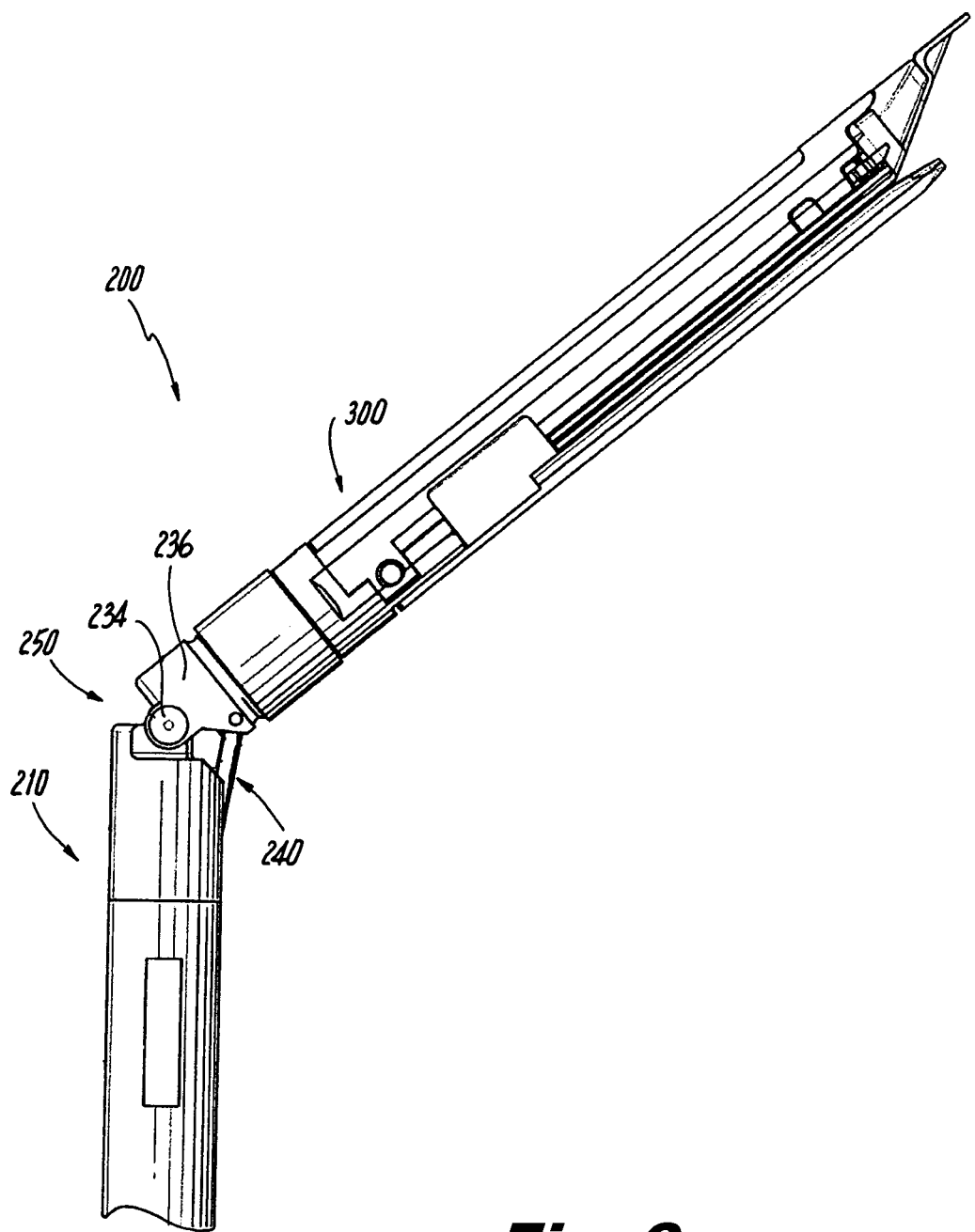
FIG. 9 is an elevational view of a distal end of a shaft assembly and an end effector secured thereto, for another endoscopic surgical device.
Figure 10:
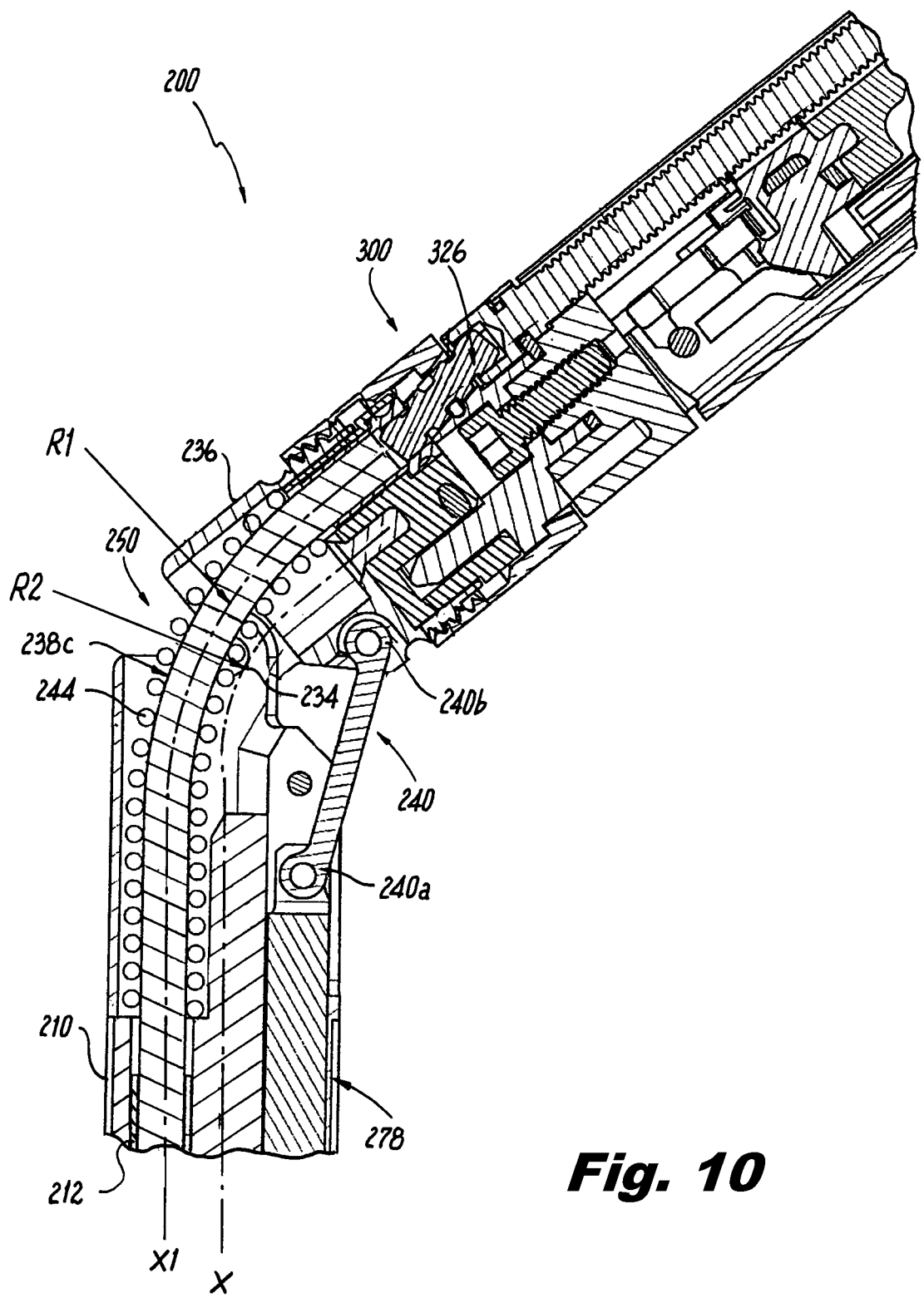
FIG. 10 is a longitudinal, cross-sectional view of the distal end of the shaft assembly and the end effector for the endoscopic surgical device of FIG. 9.

Turning now to FIGS. 9 and 10, an articulation joint 250, in accordance with the principles of the present disclosure, may be incorporated into an endoscopic surgical device in the form of an endoscopic surgical stapler 200. Endoscopic surgical stapler 200 may be in the form of an electromechanical, hand-held, powered surgical system including an electromechanical, hand-held, powered surgical instrument that is configured for selective attachment thereto of a plurality of different end effectors (including a surgical stapler), via a shaft assembly, that are each configured for actuation and manipulation by the electromechanical, hand-held, powered surgical instrument. Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire content of each of which being incorporated herein by reference, for a detailed description of the construction and operation of an exemplary electromechanical, hand-held, powered surgical instrument.

Endoscopic surgical stapler 200 includes an endoscopic shaft assembly 210 having an articulation joint 250, and a flexible drive cable 238c, extending through articulation joint 250, to effectuate a closure and a firing of an end effector 300.

Flexible drive cable 238c is fabricated from a torsionally stiff and flexible material, such as, for example, stainless steel. Flexible drive cable 238c defines a central longitudinal axis "X1" off-set a radial distance "r" from a central longitudinal axis "X" of shaft assembly 210. Flexible drive cable 238c includes a proximal end that is coupled to a distal end of rotatable drive shaft 212. Flexible drive cable 238c includes a distal end that is coupled to a rotation nut, wherein rotation of flexible drive cable 238c results in corresponding rotation of the rotation nut.

The central longitudinal axis "X1" of intermediate flexible drive cable 138c is off-set from the central longitudinal axis "X" of proximal tube portion 130a of anchor retaining/advancing assembly 130 in a direction away from a direction of articulation of articulation joint 150, or in a direction away from articulation link 152.

Articulation joint 250 includes an articulation link 240 having a proximal end 240a and a distal end 240b. Proximal end 240a of articulation link 240 is pivotally connected to a distal end of an articulation bar 278. A distal end 240b of articulation link 240 is pivotally connected to a distal neck housing 236 of an endoscopic shaft assembly 210, at a location offset a radial distance from the longitudinal axis "X" of shaft assembly 210.

Distal neck housing 236 is configured and adapted for selective connection with an end effector 300.

Shaft assembly 210 may include a reinforcing coil spring 244 surrounding flexible drive cable 238c. Reinforcing coil spring 244 functions to help keep flexible drive cable 238c from kinking during articulation of end effector 300. Reinforcing coil spring 244 also functions to help keep flexible drive cable 238c from failing due to unwinding and/or "pig tailing" during rotation thereof.

In operation, as flexible drive cable 238c is rotated, due to a rotation of first rotatable proximal drive shaft 212, said rotation is transmitted, through flexible drive cable 238c, to the distal end of flexible drive cable 238c and on to the rotation nut. With end effector 300 coupled to distal neck housing 236 of shaft assembly 210, and specifically, with a drive screw of end effector 300 coupled thereto via a drive axle 326, said rotation results in actuation of end effector 300.

Also in operation, upon an axial translation of articulation bar 278, for example in a proximal direction, articulation bar 278 acts on articulation link 240 to cause articulation link 240 to translate in a proximal direction. As articulation link 240 is axially translated in a proximal direction, articulation link 240 acts on distal neck housing 236 to cause distal neck housing 236 to pivot about a pivot axis of pivot pin 234. As distal neck housing 236 is pivoted, distal neck housing 236 acts on end effector 300 to articulate end effector 300 relative to the longitudinal axis "X" of shaft assembly 210.

As such, as seen in FIG. 10, when end effector 300 is in an angled orientation, a radius of curvature "R1" of flexible drive cable 238c is relatively greater than a radius of curvature "R2" of a comparable flexible drive cable that would be located along the central longitudinal axis "X" of shaft assembly 210.

In this manner, by providing for a larger radius of curvature "R1" for flexible drive cable 238c, it is contemplated, in accordance with the present disclosure, that a flexible drive cable 238c having a relatively larger diameter or constructed from a relatively stiffer material can be used, as compared to any comparable flexible drive cable that would be located along the central longitudinal axis "X" of shaft assembly 210.

In so doing, relatively greater torsional forces, and more accurate rotation, can be transmitted along flexible drive cable 238c as compared to any comparable flexible drive cable that would be located along the central longitudinal axis "X" of shaft assembly 210.

Flexible drive cable 238c may have an outer diameter of about 0.08".

Shaft assembly 210 has an outer diameter of about 0.22". A ratio of the outer diameter of the flexible drive cable 238c to the outer diameter of shaft assembly 210 about 2.8.

Reference may be made to U.S. patent application Ser. No. 13/799,379, filed on Mar. 13, 2013, entitled "Apparatus for Endoscopic Procedures", the entire content of which is incorporated herein by reference, for a detailed discussion of the construction and operation of shaft assembly 210 and end effector 300.

Reference may be made to U.S. patent application Ser. No. 13/280,898, filed on Oct. 25, 2011, entitled "Apparatus for Endoscopic Procedures", the entire content of which is incorporated herein by reference, for a detailed discussion of the construction and operation of end effector 300. End effector 300 may be configured and adapted to apply a plurality of linear rows of fasteners, which in embodiments may be of various sizes, and which, in certain embodiments may have various lengths or rows, e.g., about 30, 45 and 60 mm in length.

In accordance with the present disclosure, it is contemplated that handle assembly 100 may be replaced by an electromechanical control module configured and adapted to drive the flexible drive cables to fire or actuate the surgical device. The electromechanical control module may include at least one microprocessor, at least one drive motor controllable by the at least one microprocessor, and a source of power for energizing the at least one microprocessor and the at least one drive motor.

It will be understood that various modifications may be made to the embodiments disclosed herein. For example, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of preferred embodiments. Those skilled in the art will envision other modifications within the scope and spirit of the claims appended thereto.

What is claimed is:

1. An endoscopic surgical device, comprising:
   a handle assembly including a handle housing and a trigger operatively connected to the handle housing, and a drive mechanism actuatable by the trigger;
   an endoscopic anchor retaining/advancing assembly extending from the handle assembly, the endoscopic anchor retaining/advancing assembly including:
      a proximal tube portion and a distal tube portion pivotably connected to one another at an articulation joint, each of the proximal tube portion and the distal tube portion defining a central longitudinal axis;
      a stiffener tube slidably disposed within the proximal tube portion;
      an inner shaft assembly rotatably disposed within stiffener tube, the inner shaft assembly including:
         a proximal inner shaft rotatably disposed within the stiffener tube, the proximal inner shaft mechanically connected to the drive mechanism such that actuation of the trigger results in rotation of the proximal inner shaft;
         a distal inner shaft rotatably disposed within the distal tube portion;
         an intermediate drive cable mechanically interconnecting the proximal inner shaft and the distal inner shaft, wherein the intermediate drive cable is relatively flexible as compared to the proximal inner shaft and the distal inner shaft, wherein the intermediate drive cable extends from and between the proximal tube portion and the distal tube portion, across the articulation joint, wherein the intermediate drive cable defines a central longitudinal axis and wherein the central longitudinal axis of the intermediate drive cable is off-set a radial distance from the central longitudinal axis of the proximal tube portion and the distal tube portion;
      an articulation link including a proximal end pivotally connected to a distal end of the stiffener tube and a distal end pivotally connected to the distal tube portion; and
      at least one fastener loaded in the distal tube portion, wherein the at least one fastener is acted upon by the distal inner shaft upon an actuation of the trigger.

2. The endoscopic surgical device according to claim 1, wherein the distal tube portion is articulatable between a non-articulated orientation and a plurality of articulated orientations relative to the proximal tube portion.

3. The endoscopic surgical device according to claim 2, wherein the central longitudinal axis of the proximal tube portion and the central longitudinal axis of the distal tube portion define a central radius of curvature for each articulated orientation of the distal tube portion relative to the proximal tube portion, and wherein the central longitudinal axis of the intermediate drive cable defines a radius of curvature that is greater than the central radius of curvature for each articulated orientation of the distal tube portion relative to the proximal tube portion.

4. The endoscopic surgical device according to claim 2, wherein the central longitudinal axis of the intermediate drive cable is off-set from the central longitudinal axis of the proximal tube portion and the central longitudinal axis of the distal tube portion in a direction away from a direction of articulation of the distal tube portion relative to the proximal tube portion.

5. The endoscopic surgical device according to claim 1, wherein the intermediate drive cable has an outer diameter of 0.08".

6. The endoscopic surgical device according to claim 1, wherein the intermediate drive cable has an outer diameter of 0.08"; and wherein the proximal tube portion and the distal tube portion each have an outer diameter of 0.22".

7. The endoscopic surgical device according to claim 1, wherein a ratio of an outer diameter of the intermediate flexible drive cable to an outer diameter of either the proximal tube portion or the distal tube portion is 2.8.

8. An endoscopic surgical device, comprising:
   an endoscopic anchor retaining/advancing assembly including:
      a proximal tube portion and a distal tube portion pivotably connected to one another at an articulation joint, each of the proximal tube portion and the distal tube portion defining a central longitudinal axis;
      a stiffener tube slidably disposed within the proximal tube portion;
      an inner shaft assembly rotatably disposed within stiffener tube, the inner shaft assembly including:
         a proximal inner shaft rotatably disposed within the stiffener tube, the proximal inner shaft mechanically connected to a drive mechanism such that actuation of the drive mechanism results in rotation of the proximal inner shaft;
         a distal inner shaft rotatably disposed within the distal tube portion; and
         an intermediate drive cable mechanically interconnecting the proximal inner shaft and the distal inner shaft, wherein the intermediate drive cable is relatively flexible as compared to the proximal inner shaft and the distal inner shaft, wherein the intermediate drive cable extends from and between the proximal tube portion and the distal tube portion, across the articulation joint, wherein the intermediate drive cable defines a central longitudinal axis and wherein the central longitudinal axis of the intermediate drive cable is off-set a radial distance from the central longitudinal axis of the proximal tube portion and the distal tube portion.

9. The endoscopic surgical device according to claim 8, wherein the distal tube portion is articulatable between a non-articulated orientation and a plurality of articulated orientations relative to the proximal tube portion.

10. The endoscopic surgical device according to claim 9, wherein the central longitudinal axis of the proximal tube portion and the central longitudinal axis of the distal tube portion define a central radius of curvature for each articulated orientation of the distal tube portion relative to the proximal tube portion, and wherein the central longitudinal axis of the intermediate drive cable defines a radius of curvature that is greater than the central radius of curvature for each articulated orientation of the distal tube portion relative to the proximal tube portion.

11. The endoscopic surgical device according to claim 9, wherein the central longitudinal axis of the intermediate drive cable is off-set from the central longitudinal axis of the proximal tube portion and the central longitudinal axis of the distal tube portion in a direction away from a direction of articulation of the distal tube portion relative to the proximal tube portion.

12. The endoscopic surgical device according to claim 8, wherein the intermediate drive cable has an outer diameter of 0.08".

13. The endoscopic surgical device according to claim 8, wherein the intermediate drive cable has an outer diameter of 0.08"; and wherein the proximal tube portion and the distal tube portion each have an outer diameter of 0.22".

14. The endoscopic surgical device according to claim 8, wherein a ratio of an outer diameter of the intermediate flexible drive cable to an outer diameter of either the proximal tube portion or the distal tube portion is 2.8.

15. The endoscopic surgical device according to claim 8, further comprising at least one fastener loaded in the distal tube portion, wherein the at least one fastener is acted upon by the distal inner shaft upon an actuation of the drive mechanism.

16. The endoscopic surgical device according to claim 8, further comprising an articulation link including a proximal end pivotally connected to a distal end of the stiffener tube and a distal end pivotally connected to the distal tube portion.

17. The endoscopic surgical device according to claim 8, wherein the stiffener tube is concentric with the proximal tube portion.

18. The endoscopic surgical device according to claim 1, wherein the stiffener tube is concentric with the proximal tube portion.

* * * * *